(12) United States Patent
Mamada et al.

(10) Patent No.: US 9,718,121 B2
(45) Date of Patent: Aug. 1, 2017

(54) CASTING INVESTMENT COMPOSITION AND CASTING PROCESS USING SAME

(71) Applicant: YOSHINO GYPSUM CO., LTD., Tokyo (JP)

(72) Inventors: Emi Mamada, Tokyo (JP); Kenichi Sugano, Tokyo (JP); Masato Yoshikane, Tokyo (JP)

(73) Assignee: YOSHINO GYPSUM CO., LTD., Tokyo (JP)

( * ) Notice: Subject to any disclaimer, the term of this patent is extended or adjusted under 35 U.S.C. 154(b) by 241 days.

(21) Appl. No.: 14/403,805

(22) PCT Filed: Jun. 17, 2013

(86) PCT No.: PCT/JP2013/066618
§ 371 (c)(1),
(2) Date: Nov. 25, 2014

(87) PCT Pub. No.: WO2013/191141
PCT Pub. Date: Dec. 27, 2013

(65) Prior Publication Data
US 2015/0136350 A1 May 21, 2015

(30) Foreign Application Priority Data

Jun. 18, 2012 (JP) ................................. 2012-136867

(51) Int. Cl.
| | |
|---|---|
| B22C 1/08 | (2006.01) |
| A61C 13/20 | (2006.01) |
| B22C 1/18 | (2006.01) |
| B22C 7/02 | (2006.01) |
| B22C 9/04 | (2006.01) |
| A61C 13/083 | (2006.01) |

(52) U.S. Cl.
CPC .............. B22C 1/08 (2013.01); A61C 13/20 (2013.01); B22C 1/181 (2013.01); B22C 1/185 (2013.01); B22C 7/02 (2013.01); B22C 9/04 (2013.01); A61C 13/083 (2013.01)

(58) Field of Classification Search
CPC ......... A61C 13/083; A61C 13/20; B22C 1/08; B22C 1/181; B22C 1/185; B22C 7/02; B22C 9/04
See application file for complete search history.

(56) References Cited

U.S. PATENT DOCUMENTS

| | | | | |
|---|---|---|---|---|
| 3,303,030 A | * | 2/1967 | Preston | ...................... B22C 1/02 |
| | | | | 106/38.3 |
| 3,436,236 A | * | 4/1969 | Gamber | ................. C04B 28/146 |
| | | | | 106/38.3 |
| 4,146,670 A | * | 3/1979 | Rogers | ................... C04B 35/481 |
| | | | | 106/450 |
| 4,284,121 A | * | 8/1981 | Horton | ..................... B22C 1/167 |
| | | | | 106/38.3 |
| 4,529,028 A | * | 7/1985 | Dybala | ...................... B22C 3/00 |
| | | | | 106/38.27 |
| 4,696,455 A | * | 9/1987 | Johnson | ................. B22D 41/02 |
| | | | | 266/280 |
| 4,814,011 A | | 3/1989 | Kamohara et al. | |
| 5,373,891 A | | 12/1994 | Kato et al. | |
| 6,258,813 B1 | | 7/2001 | Arlt et al. | |
| 6,949,136 B2 | * | 9/2005 | Horton | ..................... B22C 1/185 |
| | | | | 106/38.2 |
| 2004/0256081 A1 | * | 12/2004 | Kato | ....................... B22C 1/181 |
| | | | | 164/518 |
| 2011/0159451 A1 | | 6/2011 | Kuo et al. | |
| 2015/0080207 A1 | | 3/2015 | Mamada et al. | |

FOREIGN PATENT DOCUMENTS

| | | | |
|---|---|---|---|
| DE | 19918316 A1 | * | 12/1999 |
| JP | 54-136525 | | 10/1979 |
| JP | 04037435 | | 2/1992 |
| JP | 04-330006 | | 11/1992 |
| JP | 6-336409 | | 12/1994 |
| JP | 7-164096 | | 6/1995 |
| JP | 7-103006 | | 11/1995 |
| JP | 09-192777 | | 7/1997 |
| JP | 9-220638 | | 8/1997 |
| JP | 09-299385 | | 11/1997 |
| JP | 10-113746 | | 5/1998 |
| JP | 11-76270 A | * | 3/1999 |
| JP | 11-226695 | | 8/1999 |
| JP | 2002-087918 | | 3/2002 |
| JP | 2002-235277 A | * | 8/2002 |
| JP | 2003-034608 | | 2/2003 |
| JP | 2011-500142 | | 1/2011 |
| KR | 2002-0090474 A | * | 12/2002 |

OTHER PUBLICATIONS

Korean Office Action, issued in the corresponding Korean patent application No. 10-2015-7001006, dated Nov. 30, 2015, 5 pages.

* cited by examiner

*Primary Examiner* — Anthony J Green
(74) *Attorney, Agent, or Firm* — Hamre, Schumann, Mueller & Larson, P.C.

(57) ABSTRACT

The object of the present invention is to provide an embedding material composition for casting that makes it possible to conduct a favorable casting in the case where casting is conducted using a resin pattern that is different from a conventional wax pattern in disappearance temperature and disappearance behaviors through "rapid heating" excellent in treatment efficiency. The present invention relates to an embedding material composition for casting not using a heat-expandable refractory material as a main component, comprising: a binder; and a non-heat-expandable refractory material having an average particle diameter of 5 to 20 μm as main components, in which a content of the binder is 25 to 40 parts by mass and a content of the non-heat-expandable refractory material is 60 to 75 parts by mass in the case where the total amount of the main components is 100 parts by mass, and the present invention also relates to a casting process using the embedding material composition for casting.

4 Claims, No Drawings

CASTING INVESTMENT COMPOSITION AND CASTING PROCESS USING SAME

TECHNICAL FIELD

The present invention relates to an embedding material composition for casting comprising a binder and a non-heat-expandable refractory material as main components. More specifically, the present invention relates to a gypsum-based embedding material composition for casting comprising calcined gypsum as a binder or a phosphate-based embedding material composition for casting comprising a mixture of magnesium oxide and ammonium primary phosphate as a binder. The present invention particularly relates to an embedding material composition for casting suitable for casting conducted in forming a dental prosthesis, the casting using a resin pattern obtained as an output with a 3D printer and furthermore suitable also in the case where a heating system in casting is rapid heating, and the present invention also relates to a casting process using the embedding material composition for casting.

BACKGROUND ART

In dental treatment, a prosthesis or an artificial tooth comprising a material made of a metal or the like having a complicated shape that is adaptable to each patient is generally used. As one of the processes for casting a metal that have long been conducted in manufacturing the prosthesis or the like, there is a lost wax process of precision casting. The outline of the process in the case of manufacturing the prosthesis or the like by the process is as follows. In the first place, a part (object) which a patient is in need for is shaped using an impression material, and, based on this, a dental gypsum model is made. And a technician precisely manufactures a model the shape of which is the same as the object from the dental gypsum model with wax by hand. Next, an embedding material comprising a refractory material is poured into the surroundings of the obtained wax pattern (wax model) and hardened, then heating is conducted to form a mold by causing the wax pattern to disappear (to be lost) (incineration or dewaxing). Thereafter a molten metal is poured into the space of the formed mold, and, after cooling, a cast is taken out by breaking the mold to obtain the intended prosthesis or the like having a complicated shape.

Amid the times when the image analysis technology has advanced by leaps and bounds, the following process has been developed and has been utilized in recent years. Specifically, the gypsum model manufactured in the same manner as described above is subjected to three dimensional scanning to obtain a sophisticated image data (hereinafter, also simply referred to as "image data"), the prosthesis or the like being an object is digitally portrayed on a computer (PC), and a resin pattern for the object is output as a mechanically precise stereo image with a 3D printer. It is anticipated that the technology will spread with the advance of the image analysis technology in the future, and in this case, heating is conducted using the pattern manufactured with a resin (an acrylic UV curing resin or the like) in place of the above-described wax pattern to form a mold by causing the resin pattern to disappear (to be lost), and the subsequent production processes are to be conducted.

The embedding materials that are used for the above-described wax or resin pattern are different depending on the kind of metal to be cast, and there exist a "gypsum-based embedding materials", "phosphate-based embedding materials", "silica-based embedding materials", and so on. Among these, the "gypsum-based embedding materials" are used for casting a metal having a relatively lower melting point as compared with the case of using the "phosphate-based embedding materials". More specifically, in the case where casting is conducted with a metal having a melting point of 1100° C. or less (within a range of noble metal alloy that can be melted with a gas burner) [such as, for example, palladium alloy (such as gold-palladium alloy) and silver], the "gypsum-based embedding materials" are used. Although the "gypsum-based embedding materials" are inferior to the "phosphate-based embedding materials" in casting properties at a high temperature, the "gypsum-based embedding materials" have such advantages that are excellent in a taking-out property of a cast and operability (fluidity) and provides less deformation due to residual stress and less change with time, and are widely utilized.

The "phosphate-based embedding materials" are used in the case where casting is conducted with a metal having a melting point higher than in the case where the "gypsum-based embedding materials" are applied [for example, Co—Cr (cobalt-chromium alloy), Ni—Cr (nickel-chromium alloy, and so on) each having a melting point of 1200° C. to 1400° C.]. Moreover, as in the case where the aforementioned image analysis technology is utilized, conducting casting using a resin pattern in place of a wax pattern has been increased in recent years. Since the resin pattern has a higher disappearance temperature than the wax pattern does, the "phosphate-based embedding material" that is adaptable to a metal having a higher melting point is often used among the embedding materials in the case of casting using a resin pattern.

On the other hand, the heating process in forming a mold by conducting heating to allow the wax pattern to disappear (incineration or dewaxing) (to be lost) in the production process after pouring and hardening the embedding material has been changed in recent years for the purpose of improving the treatment efficiency. Specifically, the heating process has been changed from the "usual heating" in which the temperature of an electric furnace is gradually raised from room temperature to a target temperature to the "rapid heating" in which the embedding material is placed in a furnace having a target temperature to immediately start casting. Therefore, the properties of the embedding material are required so as not to cause cracks, breakage, damage, or the like even when the rapid heating is conducted.

To meet the requirement, since the metals to be used for casting as described above each have a different coefficient of contraction when solidified, any of the embedding materials, when used, is adjusted so as to have a coefficient of expansion to compensate for the coefficient of contraction of the metal to be used. Specifically, the coefficient of expansion of the embedding material is adjusted by, for example, allowing cristobalite or quartz being a heat-expandable refractory material to contain. On the other hand, there is a problem that the embedding material should be the one that is capable of preventing the occurrence of cracks, breakage, or the like liable to occur by the expansion being too large in order for the embedding material to be applicable to the above-described rapid heating. As described previously, since the "gypsum-based embedding materials" have excellent properties but are inferior to the "phosphate-based embedding materials" in casting properties at a high temperature, the "phosphate-based embedding materials" are usually used in the case where casting is conducted through the "rapid heating" using a resin pattern. Here, the incineration temperature in the conventional technology is taken as 700 to 750° C. in the case of using a gypsum-based embedding material and 800 to 900° C. in the case of using a phosphate-based embedding material. However, even though the "phosphate-based embedding material" is used, it is not easy to keep the coefficient of expansion in the optimum state for every metal to be cast and furthermore to suppress the occurrence of cracks or the like that is liable to occur in the case where the "rapid heating" is conducted.

In such present circumstances as described above, when the "phosphate-based embedding material" or the "gypsum-based embedding material" that is adaptable favorably to the "rapid heating" using a resin pattern, particularly the "gypsum-based embedding material" that is excellent in taking out property of a cast is provided, it is extremely useful. Therefore, various proposals the object of which is to provide the above-described "phosphate-based or gypsum-based embedding material" have been made as described below. For example, as a gypsum-based embedding material that does not cause cracks, breakage, damage, or the like to occur even when the rapid heating is conducted, there is a proposal on the gypsum-based embedding material comprising, as main components, calcined gypsum, and cristobalite and quartz each having a particular average particle diameter, to which embedding material an inorganic salt and a powdered refractory material having an average particle diameter larger than the above-described average particle diameter of the cristobalite and the quartz are added as components for increasing air permeability (see, Patent Literature 1). Moreover, there is a proposal on a gypsum-based embedding material for casting comprising a heat-insulating material and hemihydrate gypsum, the gypsum-based embedding material being applicable to casting at a high temperature by adding an MgO—Al$_2$O$_3$ spinel as a heat-insulating material (see, Patent Literature 2). Moreover, there is a proposal that, by adding calcium carbonate to main components comprising hemihydrate gypsum and a heat-insulating material, the air permeability is improved and, as a result thereof, the occurrence of cracks in a mold and burrs in a cast due to generation of a gas through the decomposition of gypsum or wax in calcination at a high temperature are suppressed (see, Patent Literature 3). Moreover, there is also a proposal that, by replacing a part of quartz or cristobalite excellent in performance to compensate for the coefficient of casting contraction of a metal with tridymite in the gypsum-based embedding material or phosphate-based embedding material, the rapid heating of a dental mold is made possible, the time required for the disappearance of a wax pattern and the time required for the preheating of a mold at the time of casting are largely shortened, and casting with high precision is made possible (see, Patent Literature 4). According to the studies made by the present inventors, although the above-described tridymite the rise in the coefficient of thermal expansion of which is calmer when compared with cristobalite, the tridymite does not make any difference from the technology in which cristobalite is used in that the tridymite is a heat-expandable refractory material. Furthermore, in the field of phosphate-based embedding material, there is also a proposal on providing a phosphate-based embedding material that is resistant to heat shock without allowing fissures or cracks to occur event when the rapid heating is conducted (see, Patent Literature 5).

CITATION LIST

Patent Literature

Patent Literature 1: Japanese Patent Publication No. 7-103006

Patent Literature 2: Japanese Patent Laid-Open No. 10-113746

Patent Literature 3: Japanese Patent Laid-Open No. 2002-87918

Patent Literature 4: Japanese Patent Laid-Open No. 6-336409

Patent Literature 5: Japanese Patent Laid-Open No. 2003-34608

SUMMARY OF INVENTION

Technical Problem

Against the above-described present circumstances, the present inventors have recognized that it is extremely important to develop a "phosphate-based embedding material composition" and a "gypsum-based embedding material composition" that are particularly suitable for the case where a resin pattern is used for casting for not only further evolution of a "technology capable of outputting a mechanically precise resin pattern with a 3D printer" the evolution of which has been expected in recent years but also establishment of a technology capable of easily and sophisticatedly producing, for example, a dental prosthesis or the like having a complicated shape. Furthermore, in such occasion, when the embedding material composition of the present invention is made also adaptable to the aforementioned "rapid heating", the practical value becomes extremely high. While, according to the studies made by the present inventors, it is necessary to make the heating temperature higher in order to allow the resin pattern to completely disappear as compared in the case of causing the wax pattern to completely disappear, and, besides, the disappearance behaviors of the resin pattern become totally different from those of the wax pattern. Therefore, as described previously, although there have been studies and proposals in the past regarding the "gypsum-based embedding material": that is adaptable to the rapid heating conducted for the purpose of achieving the treatment efficiency; with which the occurrence of cracks, breakage, or the like can effectively be prevented; and with which a cast that is excellent in size accuracy, any of these technologies are developed not intended for the purpose of applying to the resin pattern and therefore cannot be applied directly to the resin pattern. Moreover, the "phosphate-based embedding materials" are capable of withstanding a higher temperature as compared with the "gypsum-based embedding materials", however the development from the standpoint of a suitable formulation particularly in the case where a resin pattern is used or a suitable formulation in the case where the "rapid heating" is conducted using the resin pattern has not been made so far.

Accordingly, the object of the present invention is to provide a novel embedding material composition for casting capable of conducting a favorable casting even in the case where a resin pattern is used. Furthermore, the object of the present invention is to provide an embedding material with which a mold in which the occurrence of cracks and breakage is suppressed can be formed even in the case where casting is conducted using a resin pattern through "rapid heating" excellent in treatment efficiency and with which a cast to be obtained becomes the one having a desired and favorable size and having a smooth and glossy surface without burrs and roughness. More specifically, the object of the present invention is to provide a novel "gypsum-based embedding material composition" or "phosphate-based embedding material composition" suitable for the case where casting is conducted using a resin pattern through "rapid heating".

Solution to Problem

The above-described objects are achieved by the following present invention. Namely, the present invention provides an embedding material composition for casting not using a heat-expandable refractory material as a main component, comprising: a binder; and a non-heat-expandable refractory material having an average particle diameter of 5 to 20 μm as main components, wherein a content of the binder is 25 to 40 parts by mass, and a content of the non-heat-expandable refractory material is 60 to 75 parts by mass in the case where the total amount of the main components is 100 parts by mass.

Examples of the preferable embodiment of the present invention include the followings. Namely, the binder is any one of calcined gypsum and a mixture of magnesium oxide and ammonium primary phosphate; the non-heat-expandable refractory material is one or more selected from the group consisting of fused silica, mullite, zircon, and alumina; the content of the binder is 25 to 35 parts by mass and the content of the non-heat-expandable refractory material is 65 to 75 parts by mass; and the embedding material composition for casting is for a dental casting.

The present invention provides, as another embodiment, a casting process using any one of the above-described embedding material compositions for casting when casting is conducted to produce a cast by a lost wax process utilizing a 3D scanning image analysis data of an object of casting and using a resin pattern for the object of casting obtained as an output with a 3D printer.

Advantageous Effects of Invention

According to the present invention, a favorable casting can be conducted particularly in the case where the present invention is applied to the resin pattern, and furthermore it becomes possible to provide an embedding material for casting with which a mold in which the occurrence of cracks, breakage, damage, or the like is suppressed is obtained in the case where casting is conducted using a resin pattern through the "rapid heating". More specifically, according to the present invention, an "embedding material composition", particularly a "gypsum-based embedding material composition" or a "phosphate-based embedding material composition" is provided with which a formed mold becomes the favorable one in which the occurrence of cracks or breakage is suppressed and with which a cast obtained using the mold becomes the favorable one that has a desired and favorable size and furthermore has a smooth and glossy surface without burrs and roughness. The embedding material composition for casting provided by the present invention is useful particularly for dental casting, and by using the embedding material composition for casting, a prosthesis for example having a complicated and sophisticated shape to be required for dental treatment can be made so as to have a required and desired size and a favorable surface state, and it becomes possible to obtain such a prosthesis in a good yield and economically.

DESCRIPTION OF EMBODIMENTS

Hereinafter, the present invention will be described in more detail giving preferable embodiments. The present inventors have made diligent studies to solve the above-described problems of the conventional technologies and, as a result thereof, have obtained a finding that the resin pattern which is a target of the present invention is obtained by a method that is totally different from the method for obtaining a conventional wax pattern and, by making use of this feature, an embedding material constituted from a totally different formulation can be made regardless of a conventional embedding material formulation. Based on the new finding, the present inventors have made diligent studies to find as a result thereof that when the embedding material composition for casting is made so as to have a formulation as specified in the present invention and casting is conducted with the embedding material composition for casting using a resin pattern through the rapid heating system, cracks or breakage does not occur in a mold and a cast the surface of which is favorable and that is excellent in size accuracy and is faithful to the required size can be obtained, and have reached the present invention. The embedding material composition for casting of the present invention becomes a "gypsum-based embedding material composition for casting" or a "phosphate-based embedding material composition for casting" depending on the kind of binder to be used, however the embedding material composition for casting of the present invention becomes excellent in the above-described properties in both cases.

Hereinafter, the details concerning how the present inventors have reached the present invention will be described. The present inventors have found the following points in the process of making diligent studies for the purpose of providing an embedding material applicable to the resin pattern and adaptable to the rapid heating. In the first place, it is considered in the conventional embedding material that it is essential that a refractory material required for improving the heat resistance of the binder be a material with which a desired coefficient of expansion is obtained for the purpose of compensating for the contraction of a metal to be used for casting, and any of the refractory materials that are used at present has been constituted so as to satisfy the requirement. On the other hand, the present inventors have found that the property of the embedding material need not necessarily be the one in which the desired coefficient of expansion is secured according to the metal to be used as has been the case with the conventional embedding materials in the case where the "resin pattern" is used for casting. And the present inventors have also found that when the characteristic point that the technology of forming the "resin pattern" has is utilized more actively, it is made possible to provide an embedding material that is more useful and is economically excellent, and have reached the present invention. Specifically, since the resin pattern is formed by a method of three-dimensionally outputting an image data with a 3D printer based on the image data of an object obtained by image processing, which is totally different from the method of forming a conventional wax pattern, the present inventors have noticed the point that it can be done extremely easily to add minor modification to the shape of the resin pattern to be output in the data processing on a PC.

More specifically, as described previously, in the case of the wax pattern, a technician forms the wax pattern of an object to be required by hand faithfully to the model from a dental gypsum model formed by taking a shape from a patient, on the other hand, in the case of the resin pattern, the dental gypsum model formed by taking a shape from a patient is subjected to three-dimensional scanning to obtain a sophisticated image data, then the image data is appropriately processed on a PC, a prosthesis or the like to be required is digitally portrayed, and thereafter the resin pattern for the object is formed by outputting a stereo image with a 3D printer, and the present inventors have found that the change of the required performance for the embedding material becomes possible by actively utilizing this feature. Namely, it is technically quite easy to create an image data taking the expansion and contraction of a metal to be used for a mold or casting into consideration in advance and to form a resin pattern based on the image data at the time of image data processing on a PC. The present inventors have recognized that this means that the refractory material can be selected from a wider range of materials regardless of the conventional common general technical knowledge that "the refractory material which is used together with the binder such as gypsum has to contain a heat-expandable refractory material such as cristobalite and quartz". The present inventors have made diligent studies from such a novel standpoint on the refractory material that is used together with the binder and, as a result thereof, have found the most suitable material formulation to reach the present invention.

The explanation of the present invention is mainly made with regard to the dental embedding material in particular, however this is a representative example, and the utilization range of the embedding material composition for casting of the present invention is not limited to the dental embedding material. It is needless to say that the embedding material composition of the present invention can be used without any differentiation also in the case where, for example, jewelry, arts and crafts, metal parts, or the like having a complicated and sophisticated shape is subjected to the precision casting. It is anticipated that the utilization of the technology of mechanically forming a sophisticated and three-dimensional resin pattern for an object applying the above-described image analysis technology will cover a wide range of fields from now on, however it is considered that the gypsum-based embedding material composition for casting or the phosphate-based embedding material composition for casting of the present invention will have great significance to the realization of the utilization.

In the conventional embedding material for casting, it is usual to use, in addition to a binder, a heat-expandable refractory material such as cristobalite and quartz as a refractory material for the purpose of improving the fire resistance and adjusting the change in size of a mold, however, in this occasion, it is known that when the expansion of the cristobalite is too large (the blending amount is too large), cracks are liable to occur. On the other hand, in the present invention, the heat-expandable refractory material such as cristobalite is not basically used as a main component of the embedding material composition, a binder and a non-heat-expandable refractory material having an average particle diameter of 5 to 20 µm are used as main components, and furthermore the combination of the main components are specified so that the content of the binder is 25 to 40 parts by mass, and the content of the non-heat-expandable refractory material is 60 to 75 parts by mass in the case where the total amount of the binder and the non-heat-expandable refractory material is 100 parts by mass. In addition, the main component in the present invention is a term versus a component that is contained as an additive and means a component other than the additive. The additives mean components which are each used so that the content is less than 5 parts by mass in the case where the total amount of the embedding material composition for casting of the present invention is 100 parts by mass. According to the studies made by the present inventors, the embedding material composition for casting of the present invention thus constituted makes it possible to conduct a favorable casting even in the case where casting is conducted with the embedding material using a resin pattern through the rapid heating, to forma mold in which the occurrence of cracks, breakage, or the like is suppressed, and to make an obtained cast so as to have a desired and favorable size and a smooth and glossy surface without burrs or roughness.

Hereinafter, the description will be made regarding each raw material that constitutes the gypsum-based or phosphate-based embedding material composition for casting (hereinafter, also simply referred to as "embedding material composition") of the present invention.
<Binder>

The binder that constitutes the embedding material composition of the present invention includes calcined gypsum (hereinafter, an embedding material composition that uses calcined gypsum will be referred to as a "gypsum-based embedding material composition") or a mixture of magnesium oxide and ammonium primary phosphate (hereinafter, an embedding material composition that uses the mixture of magnesium oxide and ammonium primary phosphate will be referred to as a "phosphate-based embedding material composition").
(Calcined Gypsum)

Calcined gypsum is a ½ hydrate of calcium sulfate [$CaSO_4 \cdot \frac{1}{2}H_2O$] and an anhydride of calcium sulfate [$CaSO_4$], and examples of the calcined gypsum include β type hemihydrate gypsum, α type hemihydrate gypsum, and calcium sulfate anhydrite III, or a mixture thereof. Any calcined gypsum can be used for the present invention, however it is more preferable to use the α type hemihydrate gypsum taking the required strength of the mold during casting into consideration. The calcined gypsum chemically reacts with water to be easily changed to dihydrate gypsum and therefore is used as a binder. Slurry obtained by adding an appropriate amount of water to the gypsum-based embedding material composition of the present invention and kneading the resultant mixture is immediately solidified when injected into a form using, as a core, a resin pattern. Thereafter, when the gypsum-based embedding material composition of the present invention is calcined at a high temperature, the resin pattern disappears to form a mold. The gypsum-based embedding material composition of the present invention uses the gypsum as a binder and therefore has advantages that: the slurry is excellent in fluidity when injected into the form; the mold to be obtained provides less deformation due to residual stress after calcination; furthermore a cast can be easily taken out after casting; and the change with time is small. The blending ratio of the calcined gypsum in the gypsum-based embedding material composition of the present invention is required that the calcined gypsum be contained in an amount of 25 to 40 parts by mass in the case where the total amount of the main components comprising the calcined gypsum and the non-heat-expandable refractory material described later is 100 parts by mass. More preferably, when the blending ratio of the calcined gypsum is adjusted to be 25 to 35 parts by mass, it becomes possible to suppress the occurrence of cracks or breakage in the formed mold more stably and favorably.
(Magnesium Oxide and Ammonium Primary Phosphate)

In the phosphate-based embedding material composition of the present invention, a mixture of magnesium oxide and ammonium primary phosphate is used as a binder. It is preferable that the magnesium oxide used in this occasion has a high purity and furthermore is micronized. Moreover, ammonium primary phosphate that is used together with the magnesium oxide is soluble, however it is preferable to use ammonium primary phosphate having a smaller maximum particle diameter when used as a binder for an embedding material. It is stated in the above-described Patent Literature 5 that the blending amount of the magnesium oxide in the embedding material is preferably set to about 5 to about 15% by mass in the whole embedding material and the blending amount of ammonium primary phosphate is preferably set to about 10 to about 20% by mass in the whole embedding material in the case where magnesium oxide and ammonium primary phosphate are used for dental casting. Also in the present invention, these points are all the same with the publicly known technology. Moreover, in the case of the conventional phosphate-based embedding material, it is general that the phosphate-based embedding material that contains quartz, cristobalite, or the like as a binder is used and that colloidal silica is used as a mixing solution when the phosphate-based embedding material is mixed, and the total expansion that is commensurate with the casting contraction of various kinds of metals is obtained by adjusting the colloidal silica concentration in the mixing solution in addition to using a heat-expandable refractory material. On the other hand, in the present invention, the non-heat-expandable refractory material having a particular average particle diameter as will be described later is used together with the above-described binder without using a heat-expandable refractory material as a main component, and these materials are used as main components and adjusted so that the content of the binder is 25 to 40 parts by mass and the content of the non-heat-expandable refractory material is 60 to 75 parts by mass in the case where the total amount of the main components is 100 parts by mass. More preferable blending amount of the binder is about 25 to about 35 parts by mass similar to the gypsum-based embedding material composition, and thereby the embedding material composition slurry that is excellent in fluidity at the time of injection into the form can be obtained. Moreover, water or a mixing solution can be used in the present invention in the same manner as in the publicly known technology also when mixing is conducted.

<Non-Heat-Expandable Refractory Material>

In the embedding material composition of the present invention, the main components are constituted from the above-described binder and the non-heat-expandable refractory material having an average particle diameter of 5 to 20 μm, and further it is required that the blending amount of the non-heat-expandable refractory material be set to 60 to 75 parts by mass in the case where the total amount of the main components comprising the binder and the non-heat-expandable refractory material is 100 parts by mass. Moreover, it is more preferable to use the non-heat-expandable refractory material having an average particle diameter of 5 to 20 μm from the standpoint of the kneading property and fluidity of the material in the case where the slurry is obtained by kneading. Furthermore, it is more preferable that the blending amount of the non-heat-expandable refractory material having an average particle diameter of 5 to 20 μm is set to about 65 to about 75 parts by mass.

As described above, the aforementioned remarkable effect of the present invention is obtained by blending the non-heat-expandable refractory material as a main component in a ratio as specified in the present invention and using the non-heat-expandable refractory material having the average particle diameter as specified in the present invention. Namely, according to the studies made by the present inventors when the average particle diameter of the non-heat-expandable refractory material that is used in this occasion is smaller than 5 μm, such defects that the cracks due to heat shock occur in the mold and the burrs occur in the cast are caused. On the other hand, when the average particle diameter of the non-heat-expandable refractory material that is used is larger than 20 μm, the roughness occurs on the surface of the cast and it becomes impossible to obtain the cast having a smooth and glossy surface state. Moreover, the heat resistance of the mold is sufficiently secured by making the blending amount of the non-heat-expandable refractory material about 60 to about 75 parts by mass in the case where the total amount of the main components is 100 parts by mass.

(Specific Examples of Non-Heat-Expandable Refractory Material)

Specific examples of the non-heat-expandable refractory material that is used in the present invention include, for example, fused silica (also referred to as silica glass, fused quartz, or quartz glass), mullite ($Al_6O_{13}Si_2$), zircon ($ZrSiO_4$), and alumina ($Al_2O_3$). One or more non-heat-expandable refractory materials selected from the group consisting of these materials can be used in both cases of gypsum-based and phosphate-based embedding materials. Any of these materials has a high melting point, exhibits excellent heat resistance, and functions as a refractory material that imparts strength to the gypsum, but is a non-heat-expandable refractory material that is different from cristobalite and quartz being heat-expandable refractory materials that have generally been used for an embedding material in the past. For this reason, since these refractory materials are not suitable for the purpose of compensating for the coefficient of contraction of a metal, these non-heat-expandable refractory materials have never been used as a main component of the embedding material in any of the gypsum-based embedding materials and the phosphate-based embedding materials. In addition, it is possible to use there heat expandable refractory materials as necessary within a range that the intended purpose of the present invention is not impaired.

(Effect of Using Non-Heat-Expandable Refractory Material as Main Component)

As described previously, the present inventors have found that it is basically unnecessary to use a heat-expandable refractory material, in other words, it is unnecessary to adjust the coefficient of heat expansion of the embedding material according to the metal to be cast particularly in the case where casting is conducted forming a mold with the "gypsum-based or phosphate-based embedding material" using a resin pattern. And the present inventors have found that when an embedding material composition comprising: calcined gypsum being a gypsum-based binder or a phosphate-based binder comprising a mixture of magnesium oxide and ammonium primary phosphate; and a non-heat-expandable refractory material having a particular particle diameter as listed above; as main components, wherein these components are blended as specified in the present invention is used, the following excellent effects are obtained. Namely, a mold that is faithful to the resin pattern and is excellent dimensional accuracy can be formed and the mold in a favorable state in which the occurrence of cracks, breakage, damage, or the like is suppressed in the case where the rapid heating is conducted can be formed by using the gypsum-based embedding material composition or the phosphate-based embedding material composition of the present invention in a precision casting process. The reason for this is that the refractory material that is used in the present invention is non-heat-expandable and therefore the cracks, breakage, damage, and the like, which have been the problem in an embedding material using a conventional heat-expandable refractory material and which have been liable to occur because the expansion of the embedding material is too large, are effectively prevented. Furthermore, by making the non-heat-expandable refractory material that is used as a main component a particular material having an average particle diameter within a range of 5 to 20 μm, the present invention makes it possible to suppress the occurrence of the cracks or the like in a mold due to heat shock in the case where the "rapid heating" is conducted and achieves that a favorable cast: in which burrs do not occur; which has a smooth and glossy surface without roughness thereon; and which has a desired size is easily obtained. Hereinafter, the details concerning how the remarkable effects have been obtained will be described taking the "gypsum-based embedding material composition" for example, however, needless to say, the present invention is not limited to the "gypsum-based embedding material composition", and the same also applies to the "phosphate-based embedding material composition".

The conventional "gypsum-based embedding material" composition comprises, for example, α type calcined gypsum, quartz, and cristobalite as main blended components each blended about one third of the total amount of the main blended components. And the coefficient of expansion of the embedding material required to compensate for the contraction of a metal is taken as "coefficient of curing expansion (at the time of being placed in a furnace)"+"coefficient of thermal expansion"="total coefficient of expansion", and it has been necessary to determine the detailed combination for each metal based on this equation. The coefficient of curing expansion is determined mainly by the expansion of the α type calcined gypsum attributable to its hydration and slightly by the expansion attributable to the swelling of the cristobalite and the quartz, on the other hand, the "coefficient of heat expansion" is determined mainly by thermal change in the cristobalite and the quartz, and it is known that the expansion of the cristobalite is the largest. Therefore, in the conventional embedding material, it has been necessary to determine the most suitable combination by adjusting appropriately the kind and the amount of the heat-expandable refractory material according to the metal to be used for casting. Particularly for the purpose of making the embedding material to be applicable to the rapid heating, it has been necessary to optimally adjust the addition amount of various types of substances in addition to the combination of the main components comprising calcined gypsum and a heat-expandable refractory material as shown in the aforementioned conventional technologies.

The present inventors have made detailed research on the difference of behaviors at the time of heating between the resin pattern and the conventional wax pattern as detailed studies in the process of their studies on the aforementioned resin pattern that has begun to be used in recent years. As a result thereof, the wax that constitutes the wax pattern has a melting point of about 100° C., therefore dewaxing is allowed to occur extremely easily by heating, and the wax is vaporized to disappear. On the other hand, the resin that constitutes the resin pattern is not easily melted when heated and is disappeared through carbonization by raising the temperature. As described here, the resin pattern and the wax pattern are totally different in the behavior at the time of heating. And since the resin, as described above, disappears through carbonization, the resin has a property that a carbide is left when the incineration is insufficient and has a property to expand at the time of disappearance, and it has also been found that the damage of the mold attributable to these properties may occur. For example, according to the studies made by the present inventors, the wax in the wax pattern has melted at around 70° C. and has completely disappeared at 560° C. via carbonization, while the resin in the resin pattern has been softened at around 420° C. (has begun to lose its shape) and has been vaporized and disappeared gradually (has become small) to completely disappear at 660° C.

The present invention has been made as a result of studies in consideration of the special characteristics of the method of forming a resin pattern and the complexity of adjusting the above-described formulation of embedding material for each metal to be cast, and the biggest feature of the present invention exists in that it is unnecessary to conduct the operation of adjusting the material for the purpose of compensating for the casting contraction of each metal that to be used for casting in determining the formulation of the embedding material. As described previously, the resin pattern as a prerequisite of the present invention is different from the wax pattern that is formed by hand faithfully to the model by a technician from a dental gypsum model formed by taking a shape from a patient, but is formed by processing a sophisticated image date obtained from the dental gypsum model utilizing the image analysis technology and outputting three-dimensionally the image data obtained by the processing with a 3D printer. Therefore, it can easily be done to take the coefficient of expansion of a metal to be used for casting into consideration in the process of obtaining the image data to be output. The embedding material composition of the present invention is the one that utilizes this point as a prerequisite, and the problem of casting contraction of a metal that occurs at the time of casting is solved by forming a resin pattern based on the image data taking, in advance, the curing contraction of a metal to be used at the time of casting and using the resin pattern. Namely, by utilizing the above-described technology, the embedding material composition of the present invention achieves to provide a cast having a desired size and a favorable surface state in a good yield although the embedding material composition of the present invention comprises, as a main component, a material not having a property with which the curing contraction of the metal can be compensated. In addition, since the embedding material composition of the present invention is the embedding material composition that is adaptable to the "rapid heating" even in the case where a resin pattern is used, it is needless to say that the embedding material composition of the present invention is also adaptable to the "rapid heating" in the case where a wax pattern that disappears more easily than the resin pattern is used. Accordingly, it goes without saying that when a technology with which a wax pattern having a shape that compensates for the casting contraction of a metal to be used for casting can be formed in the case of forming the wax pattern as in the case of forming a resin pattern, the technology is applicable to the embedding material composition of the present invention as a matter of course.

EXAMPLES

Hereinafter, the present invention will be described specifically giving Examples and Comparative Examples. Here, examples in which dental prostheses were cast using the embedding material compositions of the present invention are shown. However, these are representative examples, the range to which the embedding material composition of the present invention is applicable is not limited for dental casting but is applicable to whatever, including jewelry, arts and crafts, parts, and so on, can be cast by the lost wax process using calcined gypsum as a binder. In addition, the "parts" in the following description are based on mass unless otherwise noted.

A. Gypsum-Based Embedding Material Compositions

Examples A-1 to A-8 and Comparative Examples a-1 to a-4

Preparation of Samples

Each "gypsum-based embedding material composition" of Examples and Comparative Examples was prepared using, for each composition, each raw material the particle size of which was adjusted as listed below. In addition, the particle size measurement for each raw material described below was conducted using a Micro track HRA manufactured by Nikkiso Co., Ltd.

A binder and non-heat-expandable refractory materials to be used as main components in Examples and Comparative Examples, each particle size of which was adjusted as shown below, were prepared.

(Binder)

Calcined gypsum: an α type hemihydrate gypsum raw material (manufactured by Yoshino Gypsum Co., Ltd) was pulverized to obtain calcined gypsum having an average particle diameter of 30 μm.

(Non-Heat-Expandable Refractory Materials)

Fused Silica A: a fused silica raw material was pulverized to obtain fused silica having an average particle diameter of 3 μm.

Fused Silica B: the same fused silica raw material as used for the fused silica A was pulverized to obtain fused silica having an average particle diameter of 5 μm.

Fused Silica C: the same fused silica raw material as used for the fused silica A was pulverized to obtain fused silica having an average particle diameter of 15 μm.

Fused Silica D: the same fused silica raw material as used for the fused silica A was pulverized to obtain fused silica having an average particle diameter of 20 μm.

Fused Silica E: the same fused silica raw material as used for the fused silica A was pulverized to obtain fused silica having an average particle diameter of 35 μm.

Mullite: a mullite raw material was pulverized to obtain mullite having an average particle diameter of 15 μm.

Zircon: a zircon raw material was pulverized to obtain zircon having an average particle diameter of 15 μm.

Alumina: an alumina raw material was pulverized to obtain alumina having an average particle diameter of 15 μm.

(Manufacturing of Resin Pattern)

A crown pattern was manufactured using a crown pattern abutment tooth model of A.D.A specification testing No. 2 test specimen and was used as a resin pattern for evaluating the "gypsum-based embedding material".

<Evaluation>

(Evaluation Methods)

Each gypsum-based embedding material composition of Examples A-1 to A-3 and Comparative Examples a-1 and a-2 having a combination shown in Table 1 was manufactured using each raw material described previously. To 100 parts by mass of each of the obtained embedding material compositions, 33% of kneading water was added, and the resultant mixture was stirred in vacuum for 30 seconds to obtain slurry of each embedding material composition. And a ring having a height of 50 mm and an inner diameter of 40 mm was lined by a liner having a thickness of 0.7 mm, then the resin pattern manufactured previously was embedded therein, and the slurry prepared as described above was poured into the ring. The ring was placed in a furnace the temperature of which was raised to 720° C. after 30 minutes from the start of the mixing, moored for 40 minutes, and thereafter casting was conducted using gold-palladium alloy. With regard to the obtained mold comprising the embedding material composition and the obtained cast, the following items were each tested by the following methods and evaluated according to the following criteria.

(Evaluation Items and Evaluation Methods)

(1) Heat Shock

The occurrence of cracks in the obtained molds was visually confirmed, then the mold in which large cracks had occurred to such an extent that conducting casting was made impossible was evaluated as "Poor", the mold in which cracks had occurred to such an extent that there was no practical problem in conducting casting was evaluated as "Fair", the mold in which cracks had not occurred was evaluated as "Good", and the results are shown in Table 1.

(Surface State of Casts)

The obtained cast the surface of which was smooth and glossy was evaluated as "Good", the surface of which was rough or had burrs was evaluated as "Poor", and the results are shown in Table 1.

TABLE 1

Formulations and Evaluation Results of Gypsum-Based Embedding Material Compositions-1

|  | Examples | | | Comparative Examples | |
|---|---|---|---|---|---|
|  | A-1 | A-2 | A-3 | a-1 | a-2 |
| Calcined gypsum | 40 | 30 | 25 | 50 | 15 |
| Fused silica C(15 μm) | 60 | 70 | 75 | 50 | 85 |
| Heat shock | Good | Good | Good | Poor | Poor |
| Surface state of cast | Good | Good | Good | Poor | Poor |

As shown in Table 1, the fused silica C was used as a main component in a range of 60 to 75 parts by mass in the embedding material compositions of Examples A-1 to A-3, and it was able to be confirmed that the cracks due to heat shock did not occur in the mold and the surface of the cast became favorably smooth and glossy without burrs in any of the cases. On the other hand, in the case where the embedding material composition of Comparative Example a-1 in which the blending amount of the fused silica C was smaller than the blending amount specified in the present invention was used, the cracks occurred in the mold because of insufficient fire resistance of the mold, and the burrs occurred in the cast. Moreover, in the case where the embedding material composition of Comparative Example a-2 in which the blending amount of the fused silica C was larger than the blending amount specified in the present invention was used, the strength of the mold was insufficient and the cracks occurred also in this case.

Each gypsum-based embedding material composition of Examples A-4 to A-6 having a combination shown in Table 2 was manufactured using each raw material described previously. Evaluation was conducted in the same manner as described previously using the obtained molds and the obtained casts, and the results are shown in Table 2.

TABLE 2

Formulations and Evaluation Results of Gypsum-Based Embedding Material Compositions-2

|  | Examples | | |
|---|---|---|---|
|  | A-4 | A-5 | A-6 |
| Calcined gypsum | 30 | 30 | 30 |
| Mullite (15 μm) | 70 | — | — |
| Zircon (15 μm) | — | 70 | — |
| Alumina (15 μm) | — | — | 70 |
| Heat shock | Good | Fair | Fair |
| Surface state of cast | Good | Good | Good |

As shown in Table 2, the embedding material compositions of Examples A-4 to A-6 were examples prepared in the same manner as in Example A-2 except that other kinds of non-heat-expandable refractory materials were respectively used in place of the fused silica C used in Example A-2. As a result thereof, the embedding material of Example A-4 in which the fused silica C was replaced with the mullite did not cause the cracks due to heat shock to occur similar to the embedding material composition of Example A-2. Moreover, in the case of the embedding material compositions of Examples A-5 and A-6 in which the fused silica used in Example A-2 was replaced with zircon and alumina respectively, the occurrence of small cracks due to heat shock was recognized, however the extent of the cracks was such that there was no practical problem in casting. Moreover, in the cases where the embedding material compositions of Examples A-4 to A-6 were used, the surface of the casts became favorably smooth and glossy without burrs.

Each gypsum-based embedding material composition of Examples A-7 and A-8 and Comparative Examples of a-3 and a-4 having a combination shown in Table 3 was manufactured using each raw material described previously. Evaluation was conducted in the same manner as described previously using the obtained molds and the obtained casts respectively, and the results are shown in Table 3. In addition, the results of Example A-2 in which the fused silica C was used are also shown in Table 3.

TABLE 3

Formulations and Evaluation Results of Gypsum-Based Embedding Material Compositions-3

|  | Examples | | | Comparative Examples | |
|---|---|---|---|---|---|
|  | A-7 | A-2 | A-8 | a-3 | a-4 |
| Calcined gypsum | 30 | 30 | 30 | 30 | 30 |
| Fused silica A (3 μm) | — | — | — | 70 | — |
| Fused silica B (5 μm) | 70 | — | — | — | — |
| Fused silica C (15 μm) | — | 70 | — | — | — |
| Fused silica D (20 μm) | — | — | 70 | — | — |
| Fused silica E (35 μm) | — | — | — | — | 70 |
| Kneaded state | Good | Good | Good | Fair | Good |
| Surface state of cast | Good | Good | Good | Poor | Poor |

As shown in Table 3, the embedding material compositions of Examples A-7 and A-8 in which the fused silica B having an average particle diameter of 5 μm and the fused silica D having an average particle diameter of 20 μm were blended respectively in place of the fused silica C used in preparation of the embedding material composition of Example A-2 were obtained. Moreover, the embedding material compositions of Comparative Examples a-3 and a-4 in which the fused silica A having an average particle diameter of 3 μm and the fused silica E having an average particle diameter of 35 μm were blended respectively were obtained. As shown in Table 3, in the case where the embedding material compositions of Examples A-7 and A-8 were used, it was confirmed that there was no problem in the kneaded states and the cast is made so as to have a smooth and glossy surface similar to the case where the embedding material composition of Example A-2 was used. However, in the case of the embedding material composition of Comparative Example a-3 in which the fused silica A having an average particle diameter of 3 μm was used as a main component, the slurry at the time of kneading lacked fluidity so that it was difficult to knead the slurry, the cracks occurred in the mold, and the burrs occurred on the surface thereof. Moreover, in the case of the embedding material composition of Comparative Example a-4 in which the fused silica E having an average particle diameter of 35 μm was used as a main component, the fluidity of the slurry was favorable, however the surface of the produced cast was rough.

B. Phosphate-Based Embedding Material Compositions

Examples B-1 to B-8 and Comparative Examples b-1 to b-4

Preparation of Samples

Each "phosphate-based embedding material composition" of Examples and Comparative Examples was prepared using, for each composition, each raw material the particle size of which was adjusted as listed below. In addition, the particle size measurement for each raw material described below was conducted using a Micro track HRA manufactured by Nikkiso Co., Ltd.

(Binders)

A magnesium oxide raw material was pulverized and classified to adjust the average particle diameter so as to be 25 μm. Moreover, ammonium primary phosphate was pulverized, and these pulverized materials were used as binders. Furthermore, colloidal silica sol (the particle diameter of colloidal silica was 40 to 60 nm and the concentration was 30%) was prepared as a mixing liquid.

(Non-Heat-Expandable Refractory Materials)

Fused Silica A: a fused silica raw material was pulverized to obtain fused silica having an average particle diameter of 3 μm.

Fused Silica B: the same fused silica raw material as used for the fused silica A was pulverized to obtain fused silica having an average particle diameter of 5 μm.

Fused Silica C: a fused silica raw material was pulverized to obtain fused silica having an average particle diameter of 15 μm.

Fused Silica D: the same fused silica raw material as used for the fused silica A was pulverized to obtain fused silica having an average particle diameter of 20 μm.

Fused Silica E: the same fused silica raw material as used for the fused silica A was pulverized to obtain fused silica having an average particle diameter of 35 μm.

Mullite: a mullite raw material was pulverized to obtain mullite having an average particle diameter of 15 μm.

Zircon: a zircon raw material was pulverized to obtain zircon having an average particle diameter of 15 μm.

Alumina: an alumina raw material was pulverized to obtain alumina having an average particle diameter of 15 μm.

<Evaluation>
(Evaluation Methods)

Each phosphate-based embedding material composition of Examples B-1 to B-3 and Comparative Examples b-1 and b-2 having a combination shown in Table 4 was manufactured using each raw material described previously. To 100 parts by mass of each of the obtained embedding material compositions, 20 parts by mass of a 30% concentration colloidal silica aqueous solution was added, and the resultant mixture was stirred in vacuum for 30 seconds to obtain slurry of each embedding material composition. And a ring having a height of 50 mm and an inner diameter of 40 mm was lined by a liner having a thickness of 0.7 mm, then the resin pattern manufactured previously was embedded therein, and the slurry prepared as described above was poured into the ring. The ring was placed in a furnace the temperature of which was raised to 800° C. after 30 minutes from the start of the mixing, moored for 40 minutes, and thereafter casting was conducted using gold-palladium alloy. With regard to the obtained mold comprising the embedding material composition and the obtained cast, the following items ware each tested by the following methods and evaluated according to the following criteria.

(Evaluation Items and Evaluation Methods)

(1) Heat Shock

The occurrence of cracks in the obtained molds was visually confirmed, then the mold in which large cracks had occurred to such an extent that conducting casting was made impossible was evaluated as "Poor", the mold in which cracks had occurred to such an extent that there was no practical problem in conducting casting was evaluated as "Fair", the mold in which cracks had not occurred was evaluated as "Good", and the results are shown in Table 4.

(Surface State of Casts)

The obtained cast the surface of which was smooth and glossy was evaluated as "Good", the surface of which was rough or had burrs was evaluated as "Poor", and the results are shown in Table 4.

TABLE 4

Formulations and Evaluation Results of Phosphate-Based Embedding Material Compositions-1

| | Examples | | | Comparative Examples | |
|---|---|---|---|---|---|
| | B-1 | B-2 | B-3 | b-1 | b-2 |
| Ammonium primary phosphate | 22 | 17 | 15 | 25 | 10 |
| Magnesium oxide | 18 | 13 | 10 | 20 | 5 |
| Fused silica C (15 μm) | 60 | 70 | 75 | 55 | 85 |
| Heat shock | Good | Good | Good | Poor | Poor |
| Surface state of cast | Good | Good | Good | Poor | Poor |

As shown in Table 4, the fused silica C was used as a main component in a range of 60 to 75 parts by mass in the embedding material compositions of Examples B-1 to B-3, and it was able to be confirmed that the cracks due to heat shock did not occur in the mold and the surface of the cast became favorably smooth and glossy without burrs in any of the cases. On the other hand, in the case where the embedding material composition of Comparative Example b-1 in which the blending amount of the fused silica C was smaller than the blending amount specified in the present invention was used, the cracks occurred in the mold because of insufficient fire resistance of the mold, and the burrs occurred in the cast. Moreover, in the case where the embedding material composition of Comparative Example b-2 in which the blending amount of the fused silica C was larger than the blending amount specified in the present invention was used, the strength of the mold was insufficient and the cracks occurred also in this case.

Each phosphate-based embedding material composition of Examples B-4 to B-6 having a combination shown in Table 5 was manufactured using each raw material described previously. Evaluation was conducted in the same manner as described previously using the obtained molds and the obtained casts, and the results are shown in Table 5.

TABLE 5

Formulations and Evaluation Results of Phosphate-Based Embedding Material Compositions-2

| | Examples | | |
|---|---|---|---|
| | B-4 | B-5 | B-6 |
| Ammonium primary phosphate | | 17 | |
| Magnesium oxide | | 13 | |
| Mullite (15 μm) | 70 | | |
| Zircon (15 μm) | | 70 | |
| Alumina (15 μm) | | | 70 |
| Heat shock | Good | Fair | Fair |
| Surface state of cast | Good | Good | Good |

As shown in Table 5, the embedding material compositions of Examples B-4 to B-6 were examples prepared in the same manner as in Example B-2 except that other kinds of non-heat-expandable refractory materials were respectively used in place of the fused silica C used in Example B-2. The embedding material composition of Example B-4 in which the fused silica C was replaced with the mullite did not cause the cracks due to heat shock to occur similar to the embedding material of Example B-2. In the case of the embedding material compositions of Examples B-5 and B-6 in which the fused silica used in Example B-2 was replaced with zircon and alumina respectively, the occurrence of small cracks due to heat shock was recognized, however the extent of the cracks was such that there was no practical problem in casting. Moreover, the surface of the cast became favorably smooth and glossy without burrs in every case where any of the embedding materials was used.

Each phosphate-based embedding material composition of Examples B-7 and B-8 and Comparative Examples of b-3 and b-4 having a combination shown in Table 6 was manufactured using aforementioned respective raw materials each having a different particle diameter. Evaluation was conducted, in the same manner as described previously in examples in which the gypsum-based embedding material compositions were used, using the molds each comprising the phosphate-based embedding material composition and the casts each obtained using the phosphate-based embedding material composition, and the results are shown in Table 6. In addition, the results of Example B-2 in which the fused silica C was used are also shown in Table 6.

TABLE 6

Formulations and Evaluation Results of Phosphate-Based Embedding Material Compositions-3

| | Examples | | | Comparative Examples | |
|---|---|---|---|---|---|
| | B-7 | B-2 | B-8 | b-3 | b-4 |
| Ammonium primary phosphate | | 17 | | | |
| Magnesium oxide | | 13 | | | |
| Fused silica A (3 μm) | | | | 70 | |

TABLE 6-continued

Formulations and Evaluation Results of
Phosphate-Based Embedding Material Compositions-3

|  | Examples | | | Comparative Examples | |
| --- | --- | --- | --- | --- | --- |
|  | B-7 | B-2 | B-8 | b-3 | b-4 |
| Fused silica B (5 μm) | 70 | | | | |
| Fused silica C (15 μm) | | 70 | | | |
| Fused silica D (20 μm) | | | 70 | | |
| Fused silica E (35 μm) | | | | | 70 |
| Kneaded state | Good | Good | Good | Fair | Good |
| Surface state of cast | Good | Good | Good | Poor | Poor |

As shown in Table 6, the embedding material compositions of Examples B-7 and B-8 in which the fused silica B having an average particle diameter of 5 μm and the fused silica D having an average particle diameter of 20 μm were blended respectively in place of the fused silica C used in preparation of the phosphate-based embedding material composition of Example B-2 were obtained. As shown in Table 6, in the case where the embedding material compositions of Examples B-7 and B-8 were used, it was confirmed that there was no problem in the kneaded states and the cast is made so as to have a smooth and glossy surface similar to the case where the phosphate-based embedding material composition of Example B-2 was used. However, in the case of the embedding material composition of Comparative Example b-3 in which the fused silica A having an average particle diameter of 3 μm was used, the slurry at the time of kneading lacked fluidity so that it was difficult to knead the slurry, the cracks occurred in the mold, and the burrs occurred on the surface thereof. Moreover, in the case of the embedding material composition of Comparative Example b-4 in which the fused silica E having an average particle diameter of 35 μm was used, the fluidity of the slurry was favorable, however the surface of the produced cast was rough.

INDUSTRIAL APPLICABILITY

The present invention provides a "gypsum-based embedding material composition" or a "phosphate-based embedding material composition" that makes it possible to achieve a technology by which technology: cracks or breakage does not occur in a mold; and a favorable cast having a smooth and glossy surface without burrs and roughness thereon, the cast having a required size can be produced in a good yield in the case where a cast is manufactured using a resin pattern the evolution of which has been expected in recent years through a "rapid heating" system in which heat shock is large, the "rapid heating system" being conducted for the purpose of improving the treatment efficiency. Moreover, the "gypsum-based embedding material composition" or the "phosphate-based embedding material composition" of the present invention suitable for casting using the resin pattern can contribute not only to further evolution of a "technology capable of outputting a mechanically precise resin pattern with a 3D printer" the evolution of which has been expected in recent years but also to establishment of a technology capable of easily and sophisticatedly producing, for example, a dental prosthesis or the like having a complicated shape, and therefore the utilization thereof is expected.

The invention claimed is:

1. An embedding material composition for casting not using a heat-expandable refractory material as a main component, comprising:
   a binder; and
   a non-heat-expandable refractory material having an average particle diameter in a range from 5 to 20 μm, as main components,
   wherein the binder is calcined gypsum or a mixture of magnesium oxide and ammonium primary phosphate,
   the non-heat-expandable refractory material is one or more materials selected from the group consisting of fused silica, mullite, and zircon,
   a content of the binder is in a range from 25 to 40 parts by mass,
   a content of the non-heat-expandable refractory material is in a range from 60 to 75 parts by mass relative to a total amount of the main components as 100 parts by mass, and
   the main components in the composition consist of the binder and the non-heat-expandable refractory material, where the main component in the composition is a component included in the composition in an amount of 5 parts by mass or more relative to the composition as 100 parts by mass.

2. The embedding material composition for casting according to claim 1,
   wherein the content of the binder is in a range from 25 to 35 parts by mass, and
   the content of the non-heat-expandable refractory material is in a range from 65 to 75 parts by mass.

3. The embedding material composition for casting according to claim 1,
   wherein the embedding material composition for casting is for dental casting.

4. A process for casting, comprising:
   embedding in the embedding material composition for casting according to claim 1, a resin pattern for an object of a cast; and
   removing the resin pattern by a lost wax process so as to form a mold for the cast,
   wherein the resin pattern is formed with a 3D printer utilizing 3D scanning image analysis data of the object of the cast as an output.

* * * * *